(12) United States Patent
Wu et al.

(10) Patent No.: US 10,829,784 B2
(45) Date of Patent: *Nov. 10, 2020

(54) METHOD FOR PREPARING RECOMBINANT ADENO-ASSOCIATED VIRUS

(71) Applicant: WUHAN INSTITUTE OF PHYSICS AND MATHEMATICS, CHINESE ACADEMY OF SCIENCES, Wuhan (CN)

(72) Inventors: Yang Wu, Wuhan (CN); Fuqiang Xu, Wuhan (CN); Xiaobin He, Wuhan (CN); Kunzhang Lin, Wuhan (CN)

(73) Assignee: WUHAN INSTITUTE OF PHYSICS AND MATHEMATICS. CHINESE ACADEMY OF SCIENCES, Wuhan (CN)

( * ) Notice: Subject to any disclaimer, the term of this patent is extended or adjusted under 35 U.S.C. 154(b) by 293 days.

This patent is subject to a terminal disclaimer.

(21) Appl. No.: 15/884,329

(22) Filed: Jan. 30, 2018

(65) Prior Publication Data

US 2018/0163228 A1    Jun. 14, 2018

Related U.S. Application Data

(63) Continuation-in-part of application No. PCT/CN2016/073249, filed on Feb. 3, 2016.

(30) Foreign Application Priority Data

Jan. 20, 2016  (CN) .......................... 2016 1 0035538

(51) Int. Cl.
*C12N 15/86* (2006.01)
*C12N 7/00* (2006.01)

(52) U.S. Cl.
CPC .............. *C12N 15/86* (2013.01); *C12N 7/00* (2013.01); *C12N 2710/14043* (2013.01); *C12N 2710/14143* (2013.01); *C12N 2710/14144* (2013.01); *C12N 2750/14151* (2013.01)

(58) Field of Classification Search
None
See application file for complete search history.

(56) References Cited

U.S. PATENT DOCUMENTS

| 6,703,237 | B2 * | 3/2004 | Samulski | C12N 7/00 |
| | | | | 435/320.1 |
| 10,501,758 | B2 * | 12/2019 | Wu | C12N 7/00 |
| 2015/0307899 | A1 * | 10/2015 | Gomez Sebastian | ......... |
| | | | | C07K 14/005 |
| | | | | 800/4 |

FOREIGN PATENT DOCUMENTS

| CN | 1570121 A | * | 1/2005 |
| CN | 1570121 A | | 1/2005 |
| CN | 104388508 A | | 3/2015 |

OTHER PUBLICATIONS

WIPO machine translation for CN 1570121 (obtained from <https://patentscope.wipo.int/beta/en/search.jsf> on Jan. 6, 2020, 10 pages) (Year: 2020).*
Liu et al. (2007) "Protein Production With Recombinant Baculoviruses in Lepidopteran Larvae", from "Methods in Molecular Biology, vol. 388: Baculovirus and Insect Cell Expression Protocols, Second Edition", Humana Press Inc., Totowa, NJ, pp. 267-279 (Year : 2007).*
Aucoin et al. (2007) "Virus-like Particle and Viral Vector Production Using the Baculovirus Expression Vector System/Insect Cell System" from "Methods in Molecular Biology, vol. 388: Baculovirus and Insect Cell Expression Protocols, Second Edition", Humana Press Inc., Totowa, NJ, pp. 281-296 (Year: 2007).*
Van Beek et al. (2007) "Baculovirus Insecticide Production in Insect Larvae" from "Methods in Molecular Biology, vol. 388: Baculovirus and Insect Cell Expression Protocols, Second Edition", Edited by David W. Murhammer. Humana Press Inc., Totowa, NJ, pp. 367-378 (Year: 2007).*
Xiaobing et al. (2001) A novel method for purification of recombinant adeno-associated virus vectors on a large scale. Chinese Science Bulletin, 46(6):485-488 (Year: 2001).*
Bac-to-Bac Baculovirus Expression System: User Guide (from ThermoFisher Scientific, revised 2018, 74 pages) (Year: 2018).*
Gibson, D. (2011) Enzymatic Assembly of Overlapping DNA Fragments. Methods in Enzymology, 498:349-361, and supplementary information (Year: 2011).*
Q. Lei et al., Establishment of production system of recombinant adeno-associated viruses based on baculoviruses, Journal of Zhejiang Sci-Tech University, Sep. 2010, pp. 773-778, vol. 27, No. 5, Zhejiang Sci-Tech University, China.
G. Aslanidi et al., An inducible system for highly efficient production of recombinant adeno-associated virus (rAAV) vectors in insect Sf9 cells, Proceedings of the National Academy of Sciences of the United States of America, Mar. 31, 2009, pp. 5059-5064, vol. 106, No. 13, United States National Academy of Sciences, United States.

* cited by examiner

*Primary Examiner* — Neil P Hammell
(74) *Attorney, Agent, or Firm* — JCIP Global Inc.

(57) ABSTRACT

A method for producing recombinant adeno-associated virus, the method including: (1) transforming a gene of interest (GOI) into a recombinant baculovirus, where the recombinant baculovirus has a genome integrated with AAV Rep gene, Cap gene, and rAAV genome ITR-GOI that are needed in the production of the rAAV; and where the ITR-GOI is linked to expression cassette of the Cap gene and the Rep gene by a 5' terminal nucleic acid segment or a 3' terminal nucleic acid segment; (2) infecting host insect larvae with the recombinant baculovirus prepared in (1), such that the rAAV is produced in vivo in the host insect larvae; and (3) lysing the host insect larvae obtained in (2), and extracting and purifying the rAAV.

6 Claims, 15 Drawing Sheets
Specification includes a Sequence Listing.

SEQUENCE LISTING

```
<160> NUMBER OF SEQ ID NOS: 8

<210> SEQ ID NO 1
<211> LENGTH: 1866
<212> TYPE: DNA
<213> ORGANISM: Artificial Sequence
<220> FEATURE:
<223> OTHER INFORMATION: Fully synthetic

<400> SEQUENCE: 1
ctggcggggt tctacgaaat tgtcattaag gtcccaagcg acctggacgg gcatctgccc      60
ggcatttccg acagcttcgt gaactgggtg gccgagcagg agtgggagtt accgccagat     120
tctgacttag atctgaatct aattgagcag gcgcccctga ctgtggccga gaagctgcag     180
cgcgactttc taacggagtg gcgccgtgtg agtaaggccc cggaggccct tttctttgtg     240
caatttgaca agggagagag ctatttccac ttacacgtgc tagtggaaac caccggggtg     300
aaatccttag ttttgggacg tttcctgagt cagattcgcg aaaaactgat tcagaggatt     360
taccgcggga tcgagccgac tttgccgaac tggttcgcgg tcacaaagac cagaaacggt     420
gccggaggcg ggaacaaggt ggtcgacgag tgctacatcc ccaattattt gctcccgaaa     480
acccagcctg agctccagtg ggcctggact aatttcgaac agtacttaag cgcctgtttg     540
aatctcacgg agcgtaaacg gttggtggcg cagcatctga cgcacgtgtc gcagacgcag     600
gatcagaaca aagagaatca gaatcccaat tctgacgcgc cggtgatcag atcaaaaacg     660
tcagccaggt acatggagct agtcgggtgg ctcgtggata aggggattac ctcggagaag     720
cactggatcc aggaggacca ggcttcatac atctccttca atgcggcctc caagtcgcgg     780
tcccaaatca aggctgcgtt ggacaatgcg ggtaagatta tgagcctgac taaaaccgcc     840
cccgactatc tggtgggcca gcagcccgtg gaagacattt ccagcaatcg gatttataaa     900
attttggagc taaacgggta cgatccccaa tatgctgctt cagtctttct gggatgggcc     960
acgaaaaagt tcggcaagag gaacaccatc tggctgtttg gccctgcaac taccgggaag    1020
accaacatcg cagaggcaat agcccacact gtgcccttct acgggtgcgt aaactggacg    1080
aatgagaact tccccttcaa cgactgtgtc gacaaaatgg tgatctggtg ggaagaggg    1140
```

| | |
|---|---|
| aagatgaccg ccaaggtcgt ggagtcggcc aaagcgattc taggaggaag caaggtgcgc | 1200 |
| gtggaccaga agtgcaagtc gtcggcccag atagatccga ctcccgtgat cgtcacctcg | 1260 |
| aacacgaaca tgtgcgccgt gattgacggc aactcaacga cgttcgaaca ccagcagccg | 1320 |
| ttgcaggacc gtatgttcaa atttgaactc acccgccgtc tcgatcatga cttcgggaag | 1380 |
| gtcaccaagc aggaagtcaa ggacttcttc cggtgggcaa aggatcacgt ggttgacgtg | 1440 |
| gagcacgaat tctacgtcaa aaagggtgga gccaagaaga gaccagcccc cagtgacgca | 1500 |
| gatataagcg agccaaagcg ggtgcgagag tcagttgcgc agccatcgac gtcagacgcg | 1560 |
| aaagcttcga taaactacgc ggacaggtac caaaacaaat gttctcgaca cgtcggcatg | 1620 |
| aatctaatgc tgttcccttg cagacaatgc gagaggatga atcaaaattc gaatatctgt | 1680 |
| ttcactcacg gacagaaaga ctgtttggag tgcttgcccg tgtcagagtc tcaacctgtt | 1740 |
| tctgtcgtca agaaggcgta tcagaagctg tgctacattc atcatatcat gggcaaggtg | 1800 |
| ccggacgctt gcactgcgtg cgacctggtc aatgtagatt tggacgactg catcttcgaa | 1860 |
| caataa | 1866 |

<210> SEQ ID NO 2
<211> LENGTH: 2208
<212> TYPE: DNA
<213> ORGANISM: Artificial Sequence
<220> FEATURE:
<223> OTHER INFORMATION: Fully synthetic

<400> SEQUENCE: 2

| | |
|---|---|
| acggctgccg acggttacct acccgactgg ctcgaagaca ctctgtctga aggtataaga | 60 |
| cagtggtgga agctcaagcc tggcccaccg ccaccaaagc ctgcagagcg gcataaggac | 120 |
| gacagcagag gtcttgtgct acctgggtac aagtacctcg dacccttcaa cgggctcgac | 180 |
| aagggcgagc cggtcaacga ggcagacgcc gcggccctcg agcacgacaa agcgtacgac | 240 |
| cggcagctcg acagcggaga caatccgtac ctcaaataca accacgccga cgcggagttt | 300 |
| caggagcgcc ttaaagaaga tacgtctttt gggggcaacc tcggacgagc agtcttccaa | 360 |
| gcgaagaaga gggttcttga acctctgggc ctggtcgagg aacctgttaa dacggctccg | 420 |
| ggaaaaaaga ggccggtaga dacactcccct gtggagccag actcctcctc gggaacagga | 480 |
| aaggcgggtc agcagcctgc aagaaaaaga ttgaattttg gtcagactgg agacgcagat | 540 |
| tcagtgcctg acccccagcc tctcggacag ccgccagcag caccctctgg tctgggaact | 600 |
| aatacgatgg ctacaggcag tggcgcacca atggcagaca taacgagggg cgccgacgga | 660 |
| gtgggtaatt catcgggaaa ttggcattgc gattccacgt ggatgggaga cagagtcatc | 720 |
| accaccagca cccgaacctg ggccctgccc acctacaaca accacctcta caagcaaatt | 780 |
| tcgagccaat caggagcctc gaacgataat cactacttcg gctacagcac cccttggggg | 840 |
| tattttgatt tcaacaggtt ccactgccac ttttcaccac gtgactggca gagactcatc | 900 |
| aataacaact ggggattccg acccaagaga ctcaacttca gctctttaa cattcaagtc | 960 |
| aaggaggtca cgcagaatga cggtacgacg acgattgcca ataatcttac cagcacggtt | 1020 |
| caggtgttta ctgactcgga gtaccagctc ccgtacgtcc tcgactcggc gcatcaagga | 1080 |
| tgcctcccgc cgtttccagc agacgtattc atggtgccac agtatggata cctcaccctg | 1140 |
| aacaacggga gtcaggcagt gggacgctct tcattttact gcctggagta cttgccttct | 1200 |
| cagatgctgc gtaccggaaa caactttacc ttcagctaca cttttgagga cgtccctttc | 1260 |
| cacagcagtt acgctcacag ccagagtctg gaccgtctca tgaatccact catcgatcag | 1320 |

```
tacctgtatt acttgagcag aacaaacact ccaagtggaa caaccacgca gtcaaggctt    1380
cagttctctc aggcaggagc gagtgacatt cgggaccagt ctaggaactg gcttcctgga    1440
ccctgttacc gccagcagcg agtttcaaaa acatctgcgg ataacaacaa cagtgagtac    1500
tcttggactg gagctaccaa gtaccacctc aatggcagag actctctggt gaatccgggc    1560
ccggctatgg caagtcacaa ggacgatgaa gaaaagtttt ttcctcaaag cggagttctc    1620
atctttggga agcaaggctc agagaaaaca aatgtagaca tcgaaaaggt catgattaca    1680
gacgaagagg aaatcagaac aacaaatccc gtggctacgg agcagtatgg ttctgtatct    1740
accaacctcc agagaggcaa cagacaagcg gctacagcag atgtcaacac acaaggcgtt    1800
cttccaggca tggtttggca cgacagagat gtgtaccttc aggggcccat ctgggcaaaa    1860
attccgcaca cggacggaca ttttcacccc tctccactca tgggaggatt cggacttaaa    1920 cacctcctc cacagattct catcaagaac accccggtac ctgcaaatcc ttcgacgacc    1980
ttcagtgcgg caaagtttgc ttccttcatc acgcagtact caacgggaca ggtcagcgtg    2040
gagatcgagt gggagctgca gaaggagaac agcaagcgct ggaatcccga aattcagtac    2100
acctccaact ataacaagtc tgtcaatgtg gacttcactg tggacactaa tggcgtgtat    2160
tcagagccac gccccatagg caccagatat ctgactcgca atctgtaa              2208

<210> SEQ ID NO 3
<211> LENGTH: 141
<212> TYPE: DNA
<213> ORGANISM: Artificial Sequence
<220> FEATURE:
<223> OTHER INFORMATION: Fully synthetic

<400> SEQUENCE: 3
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac tagggggttcc t                                             141

<210> SEQ ID NO 4
<211> LENGTH: 140
<212> TYPE: DNA
<213> ORGANISM: Artificial Sequence
<220> FEATURE:
<223> OTHER INFORMATION: Fully synthetic

<400> SEQUENCE: 4
tacagctcga tatactgcgg aagtctgatc tgagcatcga ttattgtcta gctcgtcaga     60
ggcgctgaac ctatcgataa actccagaaa tgcagcctat taaccgttgc tagcctattg    120
cacgccttca gctgtcatgt                                                140

<210> SEQ ID NO 5
<211> LENGTH: 81
<212> TYPE: DNA
<213> ORGANISM: Artificial Sequence
<220> FEATURE:
<223> OTHER INFORMATION: Fully synthetic

<400> SEQUENCE: 5
gcggctcgat cgcgtattat ctagttaccg atctgaccgg aatatcacag cgcactcgtc     60
tcagcatcga tactgactac t                                               81

<210> SEQ ID NO 6
```

```
<211> LENGTH: 122
<212> TYPE: DNA
<213> ORGANISM: Artificial Sequence
<220> FEATURE:
<223> OTHER INFORMATION: Fully synthetic

<400> SEQUENCE: 6
atacggacct ttaattcaac ccaacacaat atattatagt taaataagaa ttattatcaa      60
atcatttgta tattaattaa aatactatac tgtaaattac attttattta caatcactcg     120
ac                                                                   122

<210> SEQ ID NO 7
<211> LENGTH: 128
<212> TYPE: DNA
<213> ORGANISM: Artificial Sequence
<220> FEATURE:
<223> OTHER INFORMATION: Fully synthetic

<400> SEQUENCE: 7
atcatggaga taattaaaat gataaccatc tcgcaaataa ataagtattt tactgttttc      60
gtaacagttt tgtaataaaa aaacctataa atattccgga ttattcatac cgtcccacca    120
tcgggcgc                                                             128

<210> SEQ ID NO 8
<211> LENGTH: 18
<212> TYPE: DNA
<213> ORGANISM: Artificial Sequence
<220> FEATURE:
<223> OTHER INFORMATION: Fully synthetic

<400> SEQUENCE: 8
actccggaat attaatag                                                   18
```

METHOD FOR PREPARING RECOMBINANT ADENO-ASSOCIATED VIRUS

CROSS-REFERENCE TO RELATED APPLICATIONS

This application is a continuation-in-part of International Patent Application No. PCT/CN2016/073249 with an international filing date of Feb. 3, 2016, designating the United States, now pending, and further claims foreign priority benefits to Chinese Patent Application No. 201610035538.5 filed Jan. 20, 2016. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND OF THE INVENTION

Field of the Invention

The disclosure relates to a method for preparing a recombinant adeno-associated virus (rAAV).

Description of the Related Art

Baculovirus is an enveloped double-stranded circular DNA virus that has a genome ranging from 90 to 230 kb and encodes hundreds of proteins. Currently, the baculovirus expression system is continuously perfected and developed into a widely used eukaryotic expression system. For example, Three-Bac system, Two-Bac system and One-Bac system have developed for large-scale production of recombinant adeno-associated virus (rAAV). The first generation, Three-Bac system includes three recombinant baculoviruses (BEVs): BEV/Rep, BEV/Cap and BEV/ITR-GOI which carry the AAV Rep gene, Cap gene, and rAAV genome ITR-GOI (gene of interest flanked by AAV inverted terminal repeats), respectively. However, it is not widely used because of low yield and instability especially for BEV/Rep. The second generation, Two-Bac system includes two BEVs: BEV/Cap-Rep and BEV/ITR-GOI. It has limitedly improved the rAAV yield and BEV stability. For Three- or Two-Bac systems, the rAAV could produce upon three or two BEVs infected with Sf9 cell. The third generation, One-Bac system based on Sf9/Rep-Cap packaging cell line which integrated both the Rep and Cap gene inducible expression cassettes. The rAAV could produce upon single BEV/ITR-GOI infected with Sf9/Cap-Rep packaging cell line.

The existing methods for large-scale production of rAAV by using baculovirus system all rely on infection of specific insect cell lines such as Sf9, Sf21 or Sf9/Cap-Rep cells cultured in vitro with recombinant baculoviruses. However, the disadvantages of culturing cell lines in vitro include relatively complex process steps, reaction conditions that are harsh to the equipment, and high production costs.

SUMMARY OF THE INVENTION

In view of the disadvantages or needs for improvement existing in the prior art, the disclosure provides a method for producing recombinant adeno-associated virus (rAAV). The method comprises: infecting insect larvae with a recombinant baculovirus, to produce rAAV at a large scale. The method solves the technical problems associated with the conventional methods for large-scale production of a rAAV, including the presence of relatively complex process steps, reaction conditions that are harsh to the equipment, and high production costs.

To achieve the above object, in an aspect of the disclosure, a method for producing rAAV is provided, which comprises the following steps:

(1) transforming a gene of interest (GOI) into a recombinant baculovirus, where the recombinant baculovirus has a genome integrated with AAV Rep gene, Cap gene, and rAAV genome ITR-GOI (gene of interest flanked by AAV inverted terminal repeats) that are needed in the production of the rAAV; and where the ITR-GOI is linked to expression cassettes of the Rep gene and the Cap gene by a 5' terminal nucleic acid segment or a 3' terminal nucleic acid segment;

(2) infecting host insect larvae with the recombinant baculovirus prepared in Step (1), such that the rAAV is produced in a large amount in vivo in the host insect larvae; and (3) lysing the host insect larvae obtained in (2), and extracting and purifying the rAAV.

In a class of this embodiment, (2) of the preparation method comprises:

(2-1-1): feeding hatched host insect larvae to between a 4th instar stage and a 5th instar stage;

(2-1-2): inoculating the host insect larvae obtained in Step (2-1-1) by subcutaneously injecting 10-20 μL of the recombinant baculovirus at a titer of $1 \times 10^7$ virus genome (VG)/mL to $1 \times 10^9$ VG/mL prepared in Step (1); and (2-1-3): feeding the host insect larvae injected with the recombinant baculovirus obtained in (2-1-2) until the larvae have the symptoms of appetite loss, slow movement, swollen somite, stopping feeding, and harvesting the larvae.

In a class of this embodiment, in (2-1-3) of the preparation method, the feeding is stopped before the larvae are dead when typical symptoms occur in 3 to 7 days after the host insect larvae are infected with corresponding recombinant baculovirus.

In a class of this embodiment, in the preparation method, the recombinant baculovirus is based on *Autographa californica* multiple nuclear polyhedrosis virus (AcMNPV) or *Bombyx mori* nucleopolyhedrovirus (BmNPV).

In a class of this embodiment, in the preparation method, the host insect larvae are larvae of beet armyworm (*Spodoptera exigua*) or silkworm (*Bomby xmori*).

In a class of this embodiment, in (3) of the production method, the lysing of the host insect larvae comprises specifically the step of: mashing and grinding the host insect larvae, adding a PBS solution, and homogenized, followed by 3 rounds of repeated freezing and thawing, to prepare the lysate.

In a class of this embodiment, in (3) of the preparation method, the purification comprises specifically:

centrifuging the lysate after the host insect larvae is lysed, collecting the supernatant, and extracting with chloroform, to obtain a preliminarily purified rAAV.

Compared with the prior art, the following beneficial effects are achieved with the above technical solutions conceived in the disclosure.

Compared with the in vitro culturing of insect cells, advantages of the feeding of insect larvae of the disclosure are summarized as follows: the apparatus involved is easily

DETAILED DESCRIPTION OF THE EMBODIMENTS

The invention is described in detail below with reference to the accompanying drawings and embodiments.

Figure 3:
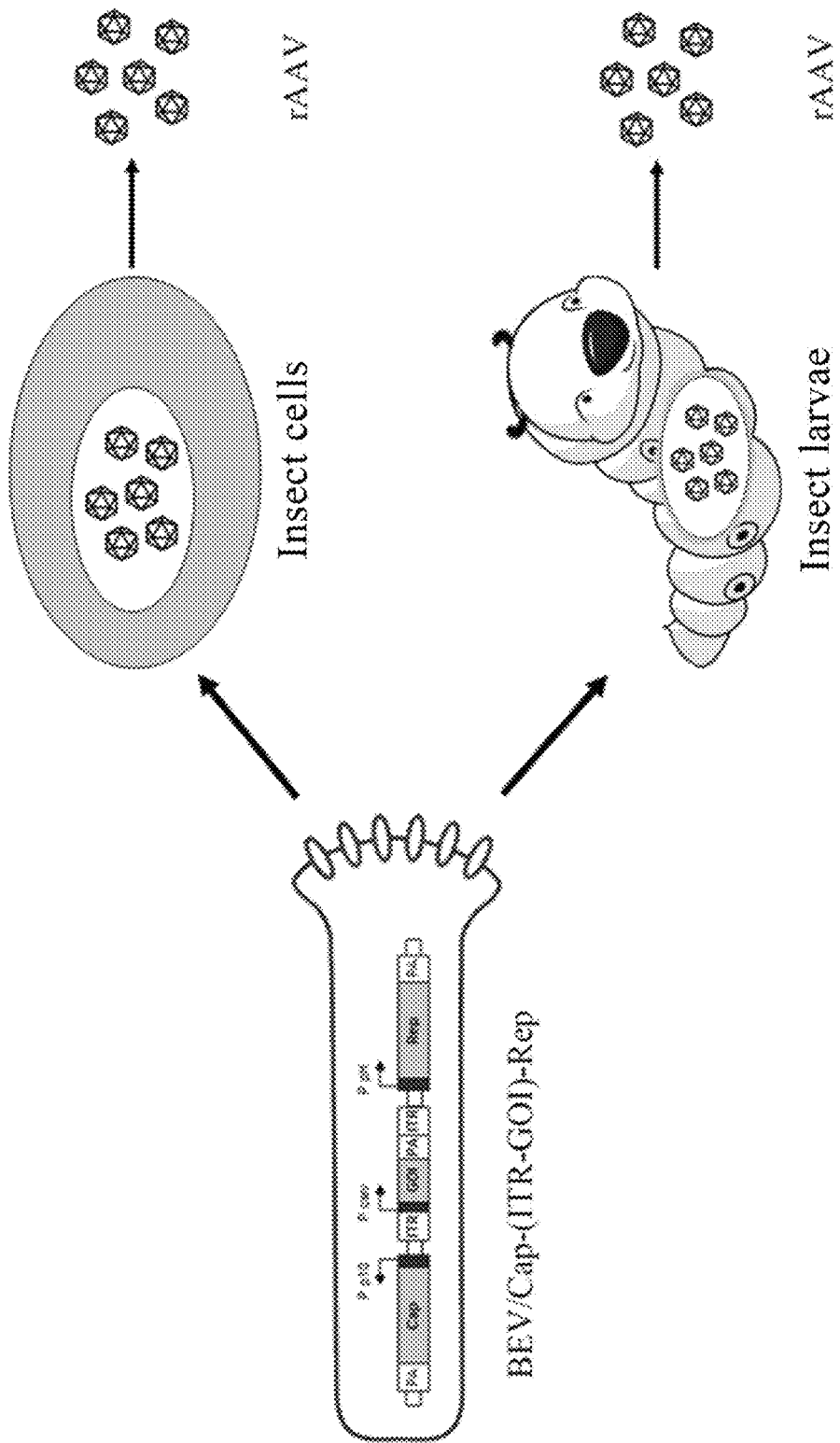
FIG. 3 is a schematic view showing a process for producing rAAV by infecting host insect cells or host insect larvae with a recombinant baculovirus in an example.

Insects are natural hosts of baculoviruses. However, the existing methods for large-scale production of rAAV by using a baculovirus system all rely on infection of specific insect cell lines cultured in vitro. Compared with the in vitro culturing of insect cells, the feeding of insect larvae has the following uncomparable advantages. The apparatus is simple, and can be easily promoted, the cost is low, the product has a high biological activity, and the production system is a natural bioreactor and has a large output. To date, no method has been developed for rAAV production by infecting insect larvae with a recombinant baculovirus. The reason is that the existing methods for producing rAAV by using a baculovirus system have the defects that are hard to overcome. In the existing Three-Bac system or Two-Bac system, since the co-infection of single insect cells with multiple recombinant baculoviruses is an inefficient random events, and the infection of insect larvae will be more uncontrollable than in vitro cultured insect cells, the efficient rAAV production cannot be achieved. In the existing One-Bac system that based on packaging cell line infected to induce the expression of the AAV Rep and Cap genes, although the construction of the packaging cell line integrated the Rep gene and Cap gene is feasible, it is difficult to construct transgenic insect larvae that similarly inducibly expresses the Rep and Cap genes. There is no reported use of a recombinant baculovirus to infect insect larvae to produce rAAV. The development of a novel One Bac system independent of a packaging cell line for rAAV production is a key prerequisite for large scale production of rAAV by infecting insect larvae with a recombinant baculovirus, as shown in FIG. 3.

*Autographa californica* multiple nuclear polyhedrosis virus (AcMNPV) or *Bombyx mori* nucleopolyhedrovirus (BmNPV) is preferred.

AcMNPV is a baculovirus that cross-infects more than 30 kinds of lepidopteran insects. Due to the specificity in infection of the hosts, AcMNPV is infectious to beet armyworm, but not silkworm. Since beet armyworm is widely distributed in the wild and can be easily fed artificially, it is one of the most commonly used host insects to study AcMNPV infection in insects (PLoS One. 2012; 7 (7): e42462). The AcMNPV-based baculovirus expression system is a baculovirus expression system that is developed earliest and most widely used (Biotechnol J. 2015 May; 10 (5): 702-14).

BmNPV is infectious to only a small range of hosts, and can infect silkworm, but not beet armyworm. Silkworm is an important economic insect. It is of a long history of thousands of years in the world to rear mulberry silkworm to produce silk and silk fabric in traditional agriculture. The BmNPV-based silkworm-baculovirus expression system has also become a widely used foreign protein expression system (ApplMicrobiolBiotechnol. 2010 January; 85(3):459-70).

The development of a new method for large-scale production of rAAV by infecting insect larvae with a recombinant baculovirus will provide a potential cost-efficient platform for the production of rAAV, one of the major viral vectors for gene therapy; and promote the fusion development of the gene therapy industry in the biomedicine economy and the insect growing industry in the traditional agricultural economy.

Figure 1:
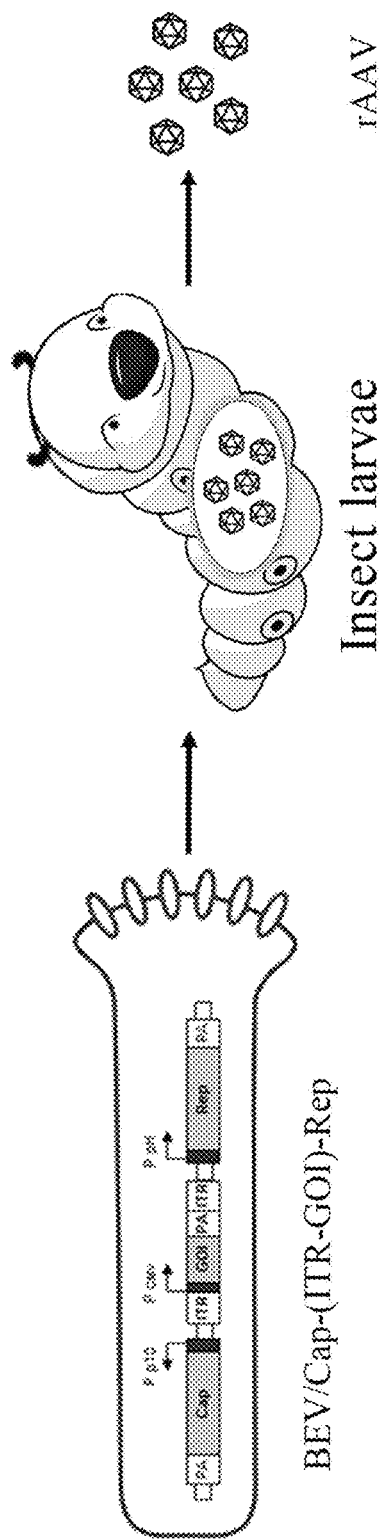
FIG. 1 is a schematic flow chart of a method for producing a rAAV provided in the disclosure.

The disclosure provides a method for producing rAAV, which comprises the following steps, as shown in FIG. 1:

(1) A gene of interest (GOI) is transformed into a recombinant baculovirus, where the recombinant baculovirus has a genome integrated with AAV Rep gene, Cap gene, and rAAV genome ITR-GOI.

The recombinant baculovirus is preferably based on the AcMNPV clone E2 (having a genome sequence deposited under Genbank accession No.: KM667940.1, Journal of virology, August 1993, p. 4566-4579), the AcMNPV clone C6 (having a genome sequence deposited under Genbank accession No.: NC_001623.1) or the BmNPV isolate T3 (having a genome sequence deposited under Genbank accession No.: L33180.1, Virologica sinica, June 2007, 22 (3): 0218-225), and integrated with a Rep gene, a Cap gene, and ITR-GOI, where the Rep gene and the Cap gene are preferably codon-optimized according to the principle of ribosomal leaky scanning.

The ITR-GOI includes an inverted terminal repeat (ITR) of the AAV genome at two ends and a gene of interest (GOI) carried in the middle portion, where the ITR-GOI is linked to an expression cassette of the Cap gene and the Rep gene by a 5' terminal nucleic acid segment or a 3' terminal nucleic acid segment. The Rep gene and the Cap gene are located upstream or downstream of the ITR-GOI.

The Rep gene is codon optimized according to the principle of ribosomal leaky scanning. An mRNA is transcribed by using a polyhedron (PH) promoter, to achieve the functional expression of Rep72 and Rep52 replication proteins. The sequence of the Rep gene is preferably as shown in SEQ ID No.: 1.

The Cap gene is also codon optimized according to the principle of ribosomal leaky scanning. An mRNA is transcripted by using a P10 promoter, to achieve the functional expression of capsid proteins VP1, VP2, and VP3 at an approximately natural ratio (1:1:10). The sequence of the Cap gene is preferably as shown in SEQ ID No.: 2.

The ITR-GOI is linked to an expression cassette of the Cap gene and the Rep gene by the ligation nucleic acid segments at two ends. ITR is an inverted terminal repeat (ITR) of the AAV genome, and preferable an ITR of AAV serotype 2, as shown in SEQ ID No.: 3. The 5' terminal or 3' terminal nucleic acid sequence is preferably a ligation nucleic acid sequence having a length ranging from 80 to 140 bp, as shown in SEQ ID No.: 4 or SEQ ID No.: 5. The ITR-GOI core expression element is a green fluorescent protein (GFP) gene expression cassette comprising a CMV promoter, a GFP gene, and a ployA (PA) component in the example, so as to facilitate the confirmation of the technical solution.

Figure 2A:
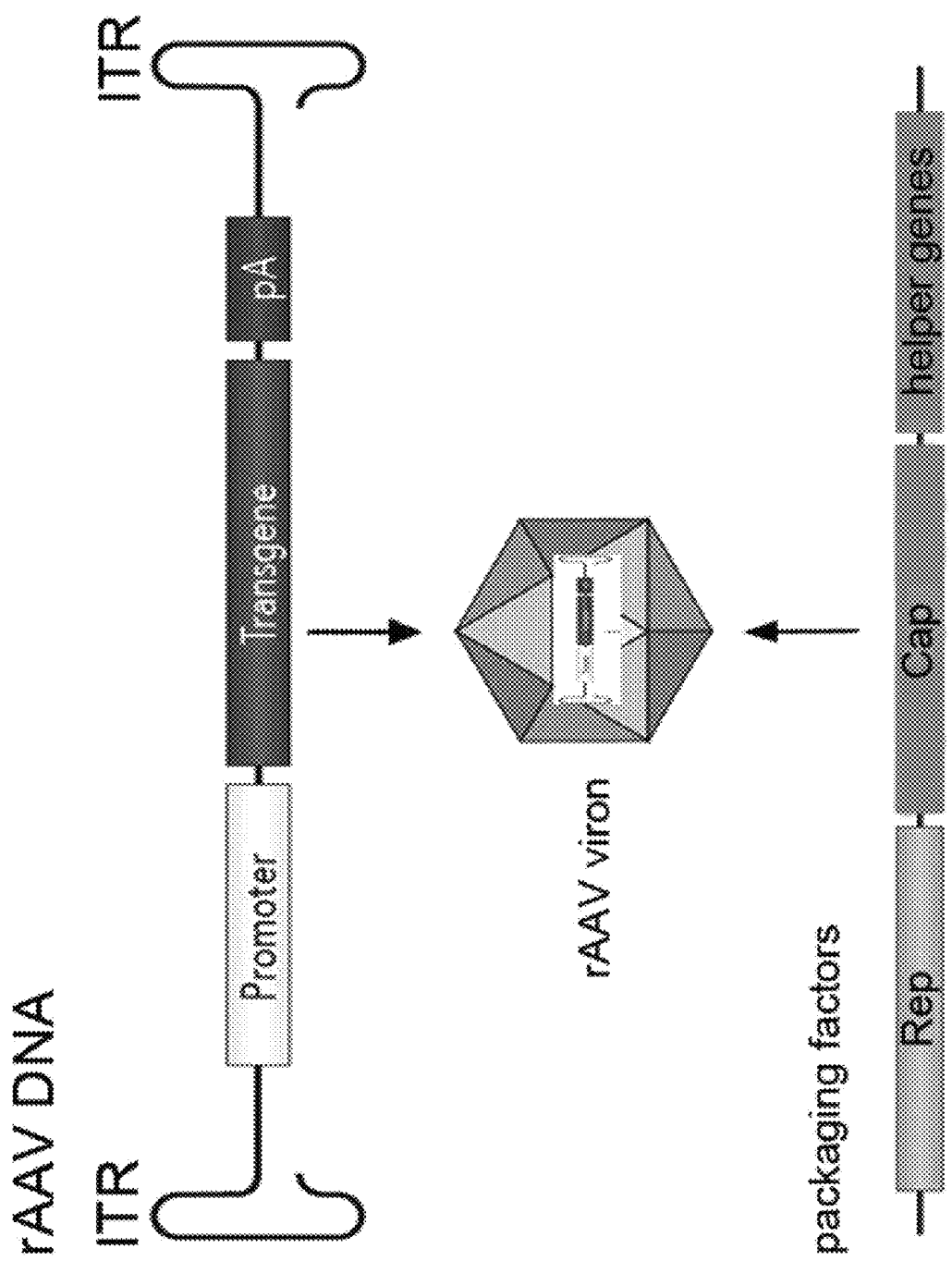
FIG. 2A shows a principle of packaging rAAV, a schematic structural view of a shuttle plasmid
Figure 2B:
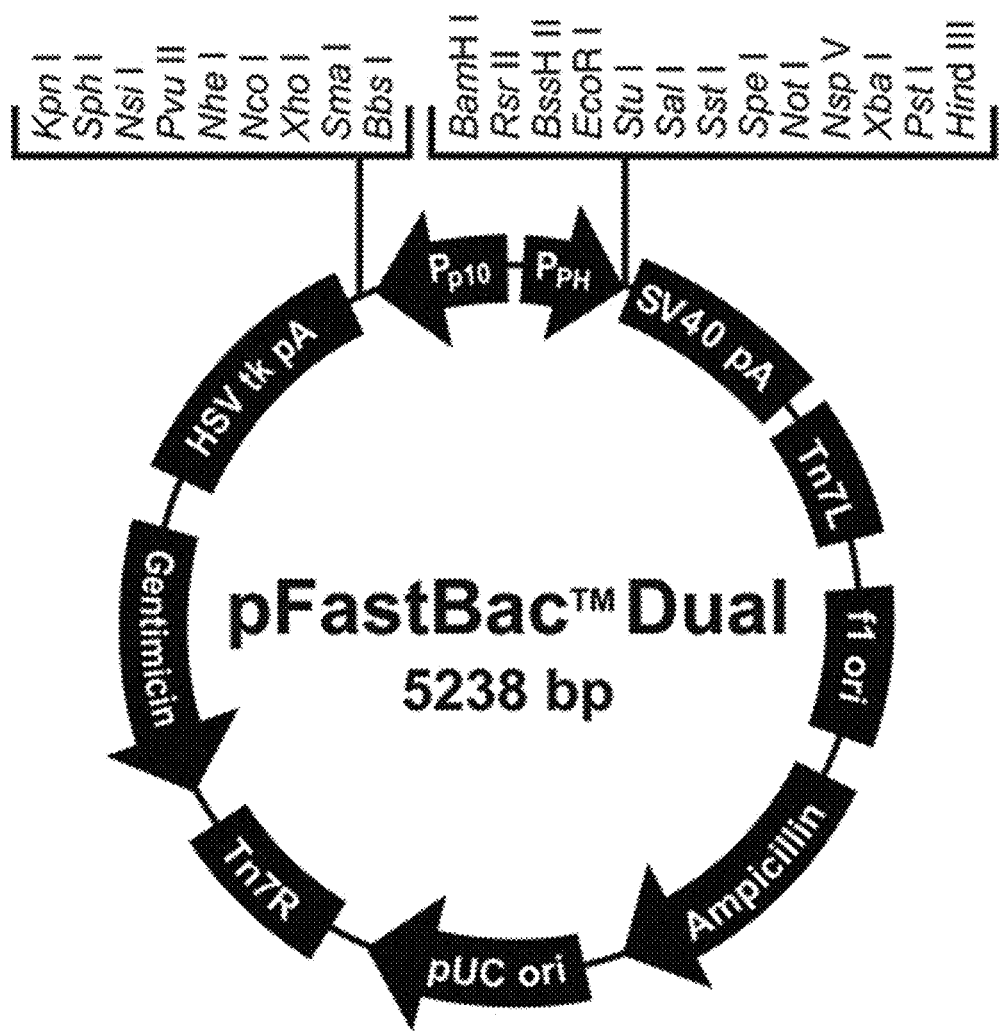
FIG. 2B shows pFast. Bac. Dual (pFBD) in a baculovirus expression system (Bac to Bac)
Figure 2C:
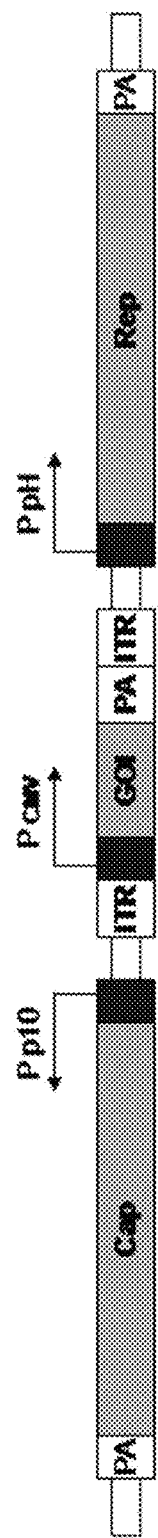
FIG. 2C shows a schematic structural view of a recombinant shuttle plasmid pFBD/Cap-(ITR-GFP)-Rep integrated with components essential for the production of the rAAV.

A combination of solutions for integrating the Rep gene, the Cap gene and the ITR-GOI into the baculovirus genome is as shown in FIG. 2C.

The recombinant baculovirus (preferably based on AcMNPV or BmNPV) provided in the disclosure can be prepared through a method comprising:

A. obtaining codon-optimized Rep gene and Cap gene by artificial gene synthesis; and obtaining an ITR-GOI by conventional molecular cloning techniques;

B. constructing the Rep gene, the Cap gene and the ITR-GOI obtained in Step A onto a shuttle plasmid pFast. Bac. Dual (pFBD) (as shown in FIG. 2B) by molecular cloning, and transfecting corresponding host Sf9 cells or BmN cells with the recombinant baculovirus genome according to the operation process of a Bac to Bac system, to obtain a corresponding recombinant baculovirus.

The genomic DNA of rAAV vector contains exogenous gene of interest which replaces the AAV coding gene and the ITR sequences which is required for virus replication and packaging. The Rep gene and the Cap gene and helper virus functions were supplied by trans-compensation for the production of rAAV, as shown in FIG. 2A.

(2) Host insect larvae are infected with the recombinant baculovirus prepared in Step (1), such that the rAAV is produced in a large amount in vivo in the host insect larvae. The infection is carried out by subcutaneous injection, and comprises specifically the following steps:

(2-1-1): feeding hatched host insect larvae to 4-5th instar larvae in a clean culture chamber with suitable temperature and humidity;

(2-1-2): inoculating the 4-5th instar host insect larvae by subcutaneously injecting the prepared recombinant baculovirus at a suitable virus dosage; and (2-1-3): feeding the host insect larvae infected with the recombinant baculovirus to allow the replication and multiplication of the virus in the larvae, until the larvae have the typical symptoms of appetite loss, slow movement, swollen somite after the virus is replicated in a large amount and generally within 3-7 days after injection, then stopping feeding, and harvesting the larvae.

(3) The insect larvae obtained in Step (2) are lysed, and the recombinant adeno-associated virus is extracted and purified.

The collected insect larvae are mashed and ground, added with a PBS solution, and homogenized, followed by 3 rounds of repeated freezing and thawing. After centrifugation for 10 min at 5000 rpm, the larvae lysate supernatant is collected, and extracted with chloroform, to obtain a preliminarily purified rAAV.

Example 1 Production of rAAV by Infecting Beet Armyworm Larvae with Recombinant Baculovirus BEV/Cap-(ITR-GFP)-Rep (1) Construction of Recombinant Baculovirus BEV/Cap-(ITR-GFP)-Rep and Verification of Virus Activity For the purpose of integrating the three main components essential for rAAV producing, that is, the AAV Cap gene, Rep gene, and the rAAV genome ITR-GOI into single recombinant baculovirus, a shuttle plasmid pFast. Bac. Dual (pFBD) in a Bac to Bac baculovirus expression system was used. In the example, the Rep gene based on AAV serotype 2 was codon optimized according to the principle of ribosomal leaky scanning, and the Rep gene was under the control of a PH promoter, so as to achieve the functional expression of Rep72 and Rep52 replication proteins. The Rep gene had a sequence as shown in SEQ ID No.: 1. In the example, the Cap gene based on AAV serotype 2 was codon optimized according to the principle of ribosomal leaky scanning, and the Cap gene was under the control of a P10 promoter, so as to achieve the functional expression of capsid proteins VP1, VP2, and VP3 at an approximately natural ratio (1:1:10). The Cap gene had a sequence as shown in SEQ ID No.: 2. In the ITR-GOI in the example, ITR was an ITR sequence of AAV serotype 2, that is, the sequence as shown in SEQ ID No.: 3, and the core expression element of ITR-GOI was an expression cassette of green fluorescent protein (GFP), where the GFP expression was controlled by a CMV promoter, for facilitating the detection of the rAAV activity. The ITR-GOI was linked to expression cassette of the Rep gene and the Cap gene by a 5' terminal nucleic acid segment and a 3' terminal nucleic acid segment. The 5' terminal or 3' terminal nucleic acid segment was a sequence as shown in SEQ ID No.: 4 (link A) or SEQ ID No.: 5 (link B).

In this example, a combination of choices of the main components in the recombinant baculovirus was as follows;

Cap-LinkA-(ITR-GFP)-linkB-Rep

A recombinant shuttle plasmid pFBD/Cap-(ITR-GFP)-Rep was constructed by placing the ITR-GFP between the P10 promoter and PH promoter of the pFBD vector via a ligation nucleic acid fragment using conventional molecular cloning techniques, as shown in FIG. 2C.

The P10 has the following sequence:

(SEQ ID No.: 6)
ATACGGACCTTTAATTCAACCCAACACAATATATTATAGTTAAATAA

GAATTATTATCAAATCATTTGTATATTAATTAAAATACTATACTGTA

AATTACATTTTATTTACAATCACTCGAC;

The PH promoter has the following sequence:

(SEQ ID No.: 7)
ATCATGGAGATAATTAAAATGATAACCATCTCGCAAATAAATAAGTA

TTTTACTGTTTTCGTAACAGTTTTGTAATAAAAAAACCTATAAATAT

TCCGGATTATTCATACCGTCCCACCATCGGGCGC;

The intermediate fragment there between has the following sequence:

(SEQ ID No.: 8)
ACTCCGGAATATTAATAG.

The recombinant shuttle plasmid was transformed into AcDH10Bac containing the AcMNPV baculovirus genome according to the Bac-to-Bac system protocol. Recombinant baculovirus genome (Bacmid) was obtained by Tn7 transposon element-mediated recombination. Positive bacteria containing recombinant Bacmid were obtained by blue-white screening and PCR identification. Recombinant Bacmid was extracted and purified and transfected into adherently cultured Sf9 cells. Sf9 cells were completely infected with recombinant baculovirus and showed obvious cytopathic effect (CPE). The cell culture was centrifuged at 3000 rpm for 5 min, and the resulting recombinant baculovirus (BEV) was contained in the supernatant.

Figure 4A:
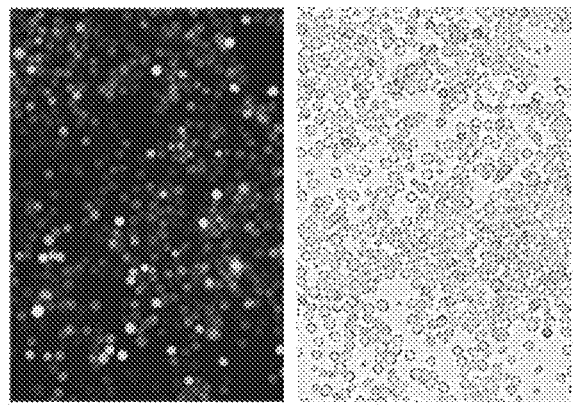
FIG. 4A is fluorescence microscopic images of Sf9 cells in Example 1 infected with the recombinant baculovirus BEV/Cap-(ITR-GFP)-Rep.
Figure 4A:
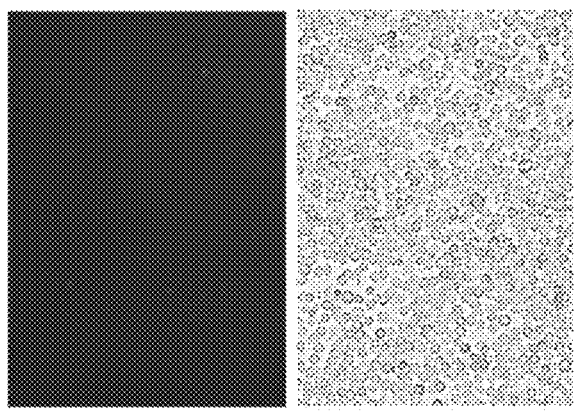

Sf9 cells in adherent culture were infected with the supernatant, and then cultured for 3 days. It was observed that the non-infected Sf9 cells in the control group grew normally, and no GFP was expressed. In contrast, in the test group, obvious cytopathogenic effect (CPE) occurred to the Sf9 cells infected with BEV, and GFP expression was obvious, as shown in FIG. 4A. This suggested that the BEV was successfully produced through the above scheme. BEV produced by transfected Sf9 cells was used to infect Sf9 cells adherently cultured or suspension cultured Sf9 cells, and the infected Sf9 cells showed CPE after 3 days; then the cell culture fluid was centrifuged at 3000 rpm for 5 min, and the BEV supernatant was obtained. The titer of the BEV was determined by the method of Fluorescent Quantitative PCR. See, ProcNatlAcadSci USA, 2009. 106 (13): 5059-64.

The cultured Sf9 cells were infected with the BEV produced in Example 1 at a multiplicity of infection (MOI) of 5. Three days after infection, the culture supernatant and cells were collected separately. The BEV was mainly secreted and released into the culture supernatant, and some un-released BEV was also present in Sf9 cells. The rAAV was mainly present in the cell nucleus. Since CPE occurred after the insect cells were infected and some cells were lysed, rAAV was also partly released into the supernatant. Therefore, BEV and rAAV were present in both the supernatant and the cells.

Figure 4B:
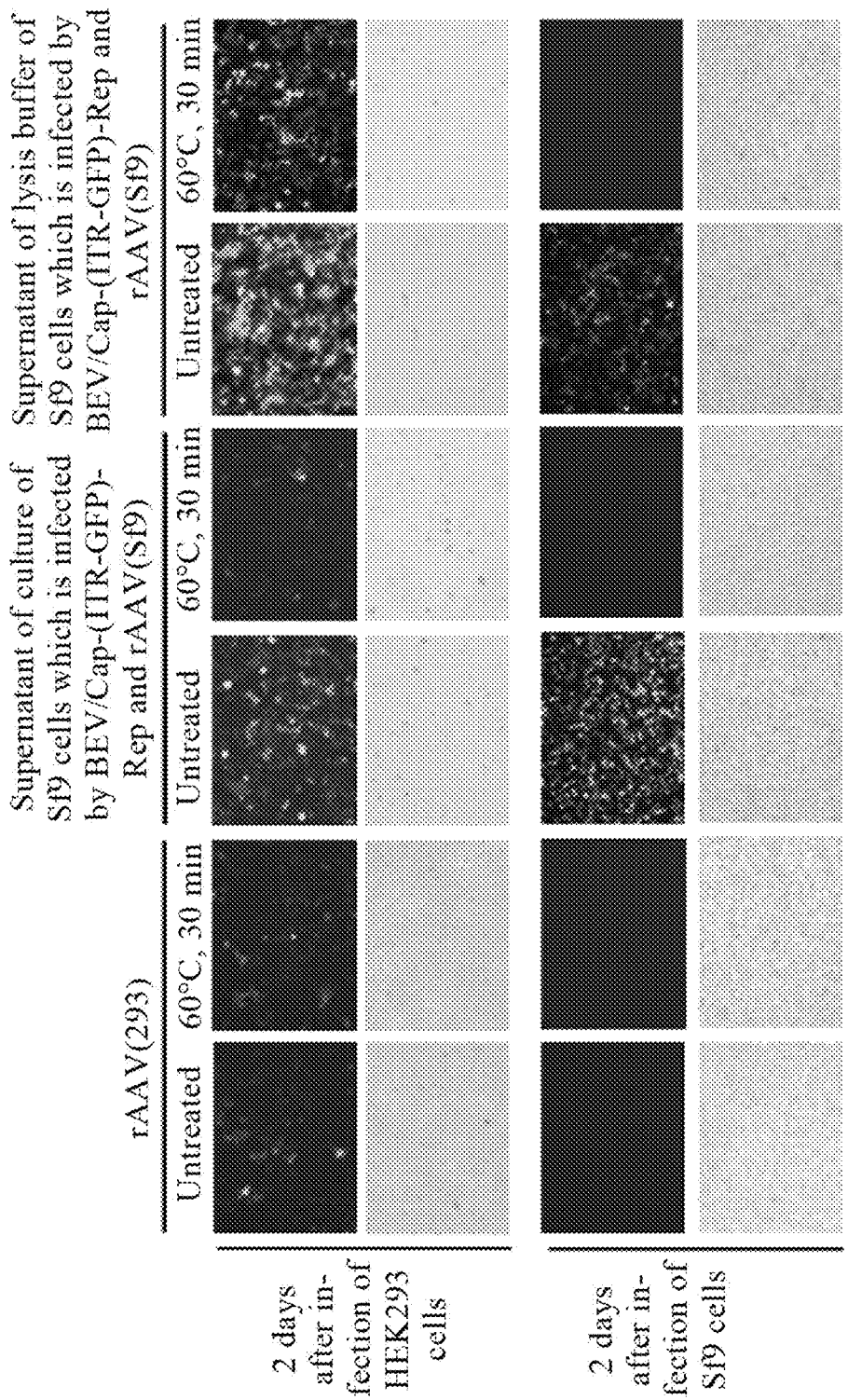
FIG. 4B is fluorescence microscopic images of HEK293 and Sf9 cells infected with the rAAV produced in Example 1.

To verify that active rAAV was produced by infecting Sf9 cells with the recombinant baculovirus, the production of rAAV with the system was experimentally confirmed by HEK293 cells and Sf9 cells based infection assays. The experimental results are shown in FIG. 4B. The detailed process and the results are as follows: The cell pellet was frozen and thawed three times for lysis, then centrifuged at 5000 rpm for 5 min and supernatant of cell lysis was collected. Because rAAV was non-enveloped, its activity was not affected by heating at 60° C. for 30 minutes, whereas recombinant baculovirus (BEV) was enveloped and lost its activity after treatment at 60° C. for 30 minutes. A simple infection-based method was used to test the rAAV activity (FIG. 4B). For rAAV2 (293 cells derived) samples, in 293 cells-based infection assays, both the treated and untreated can express GFP. In Sf9 cells-based infection assays, both the treated and untreated cannot express GFP, it indicates that rAAV2 do not infect Sf9 cells. For BEV/Cap-(ITR-GFP)-Rep supernatant samples, which contain the major secreted BEV and some rAAV. In 293 cells-based infection assays, both the treated and untreated can express GFP, while the GFP expression of the treated decrease significantly, because inactive BEV do not express GFP and only some rAAV can express GFP. In Sf9 cells-based infection assays, the untreated can express GFP, but the treated cannot express GFP. For BEV/Cap-(ITR-GFP)-Rep infected Sf9 cells lysate supernatant samples, which contain some non-secret BEVs and the major rAAV. In 293 cells-based infection assays, both the treated and untreated can express GFP, but GFP expression of the treated decrease slightly. It indicates that there is large amount of rAAVs expressing GFP. In Sf9 cells-based infection assays, the untreated can express GFP, while the treated cannot express GFP (FIG. 4B).

The results shown in FIGS. 4A-4B indicate that rAAV can be produced by infecting Sf9 cells with the recombinant baculovirus BEV/Cap-(ITR-GFP)-Rep.

(2) Production of rAAV by Infecting Beet Armyworm Larvae with Recombinant Baculovirus (BEV)

Figure 5:
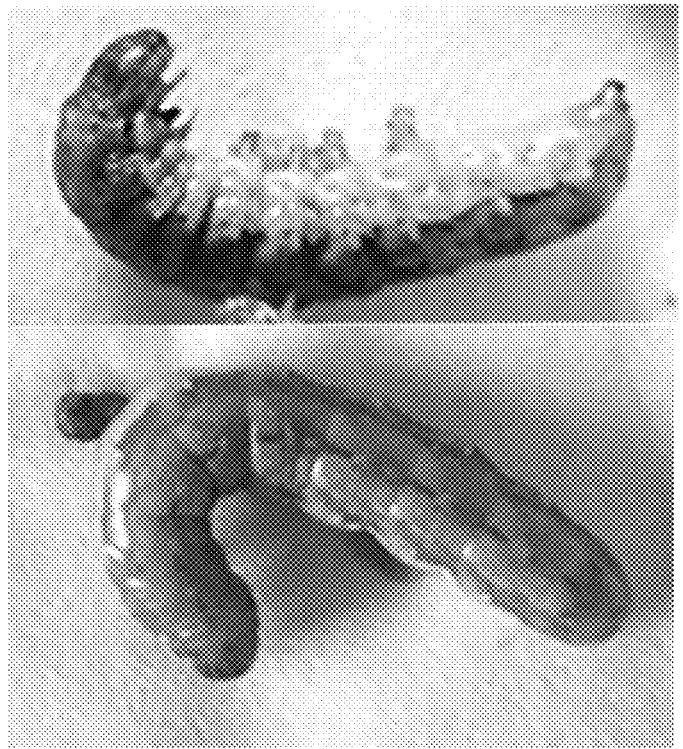
FIG. 5 shows morphologies of normal beet armyworm larvae and beet armyworm larvae having obvious pathological changes after infection with a recombinant baculovirus in Example 1.
Figure 5:
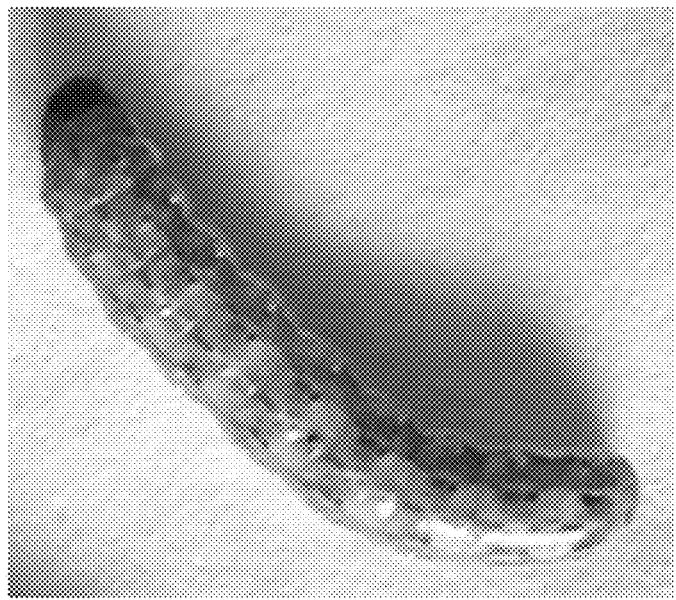

Hatched beet armyworm larvae were fed to 4-5th instar larvae. The larvae were anesthetized on ice, and inoculated by subcutaneously injecting about 10 μL recombinant baculovirus (with a BEV titer of about $1\times10^9$VG/mL) using a micro-syringe. Then, the larvae were cultured in a culture dish with a lid, and fed for additional 3-4 days. The infected host larvae had obvious pathologic symptom changes, such as appetite loss, slow movement, and swollen somite. The un-infected beet armyworm larvae grew normally (as shown in FIG. 5).

(3) Lysis of Larvae, Purification and Activity Verification of rAAV

The collected larvae were mashed and ground, added with a PBS solution, and homogenized, followed by 3 rounds of repeated freezing and thawing. After centrifugation for 10 min at 5000 rpm, the larvae lysate supernatant was collected. After the beet armyworm larvae were infected with BEV, rAAV was produced in the larvae cells while BEV was multiplied. Both BEV and rAAV were present in the larvae lysate supernatant.

Figure 6A:
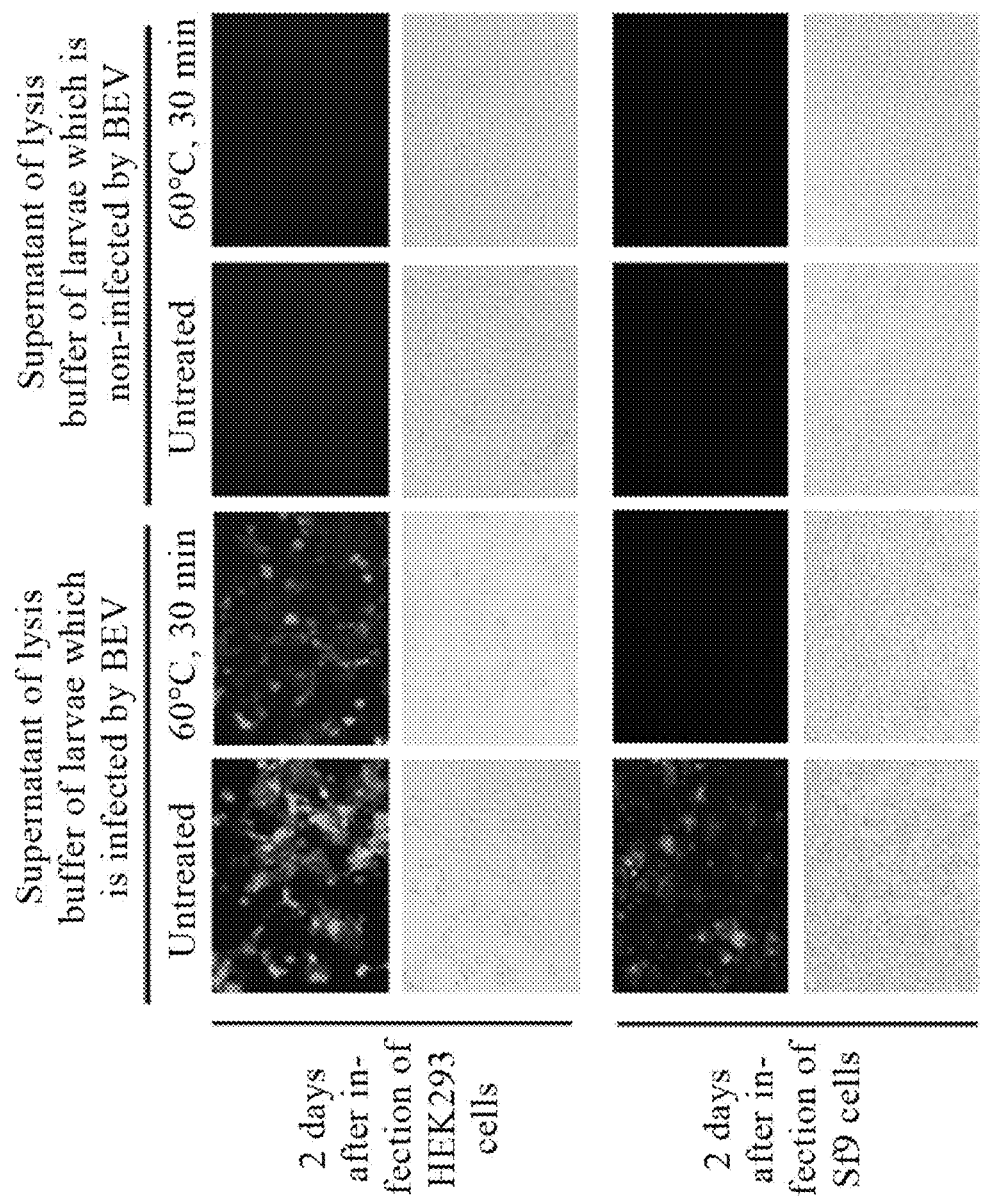
FIG. 6A is fluorescence microscopic images of HEK293 and Sf9 cells infected with a larvae lysate supernatant in Example 1.
Figure 6B:
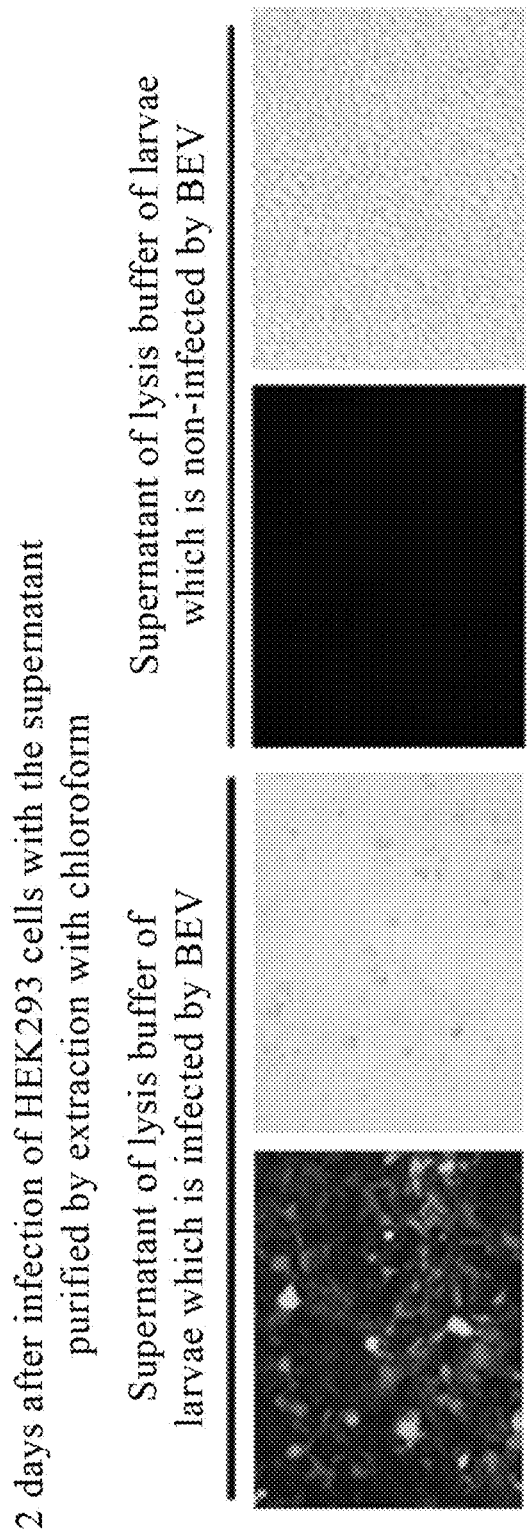
FIG. 6B is fluorescence microscopic images of HEK293 cells infected with a larvae lysate supernatant purified by extraction with chloroform in Example 1.

To verify that rAAV was produced by infecting beet armyworm larvae by injecting the recombinant baculovirus, the production of rAAV was experimentally confirmed by HEK293 cells and Sf9 cells based infection assays. The experimental results are shown in FIGS. 6A-6B. Given the fact that rAAV was non-enveloped, and the activity was not affected after 30 min-treatment at 60° C.; and the recombinant baculovirus (BEV) was enveloped, and deactivated after 30 min-treatment at 60° C., the specific implementation process and the result analysis were as follows.

For the crude uninfected larvae lysate supernatant samples, in both 293 and Sf9 cells-based infection assays, there are no GFP expression (FIG. 6A). For the crude infected larvae lysate supernatant samples, in 293 cells-based infection assays, both the treated and untreated can express GFP, but GFP expression of the treated decrease slightly. It indicates that there is large amount of rAAVs expressing GFP. In Sf9 cells-based infection assays, the untreated can express GFP, but the treated cannot express GFP (FIG. 6A).

Similar to the difference in thermo-stability, the differences in chloroform tolerance between enveloped BEV and non-enveloped AAV allowed the specific inactivation of BEV by chloroform extraction treatment. The crude larvae lysate supernatant samples were subject to chloroform extraction for 3 times. In 293 cells-based infection assays, the infected samples can express GFP, and the uninfected cannot express GFP. This result suggests that the infected samples contain rAAV tolerable for chloroform extraction treatment (FIG. 6B). The above results showed that active rAAV was successfully prepared by infecting beet armyworm larvae with the recombinant baculovirus BEV/Cap-(ITR-GFP)-Rep.

Example 2 Production of rAAV by Infecting Silkworm Larvae with Recombinant Baculovirus BEV/Cap-(ITR-GFP)-Rep (1) Construction of Recombinant Baculovirus BEV/Cap-(ITR-GFP)-Rep and Verification of Virus Activity In this example, the combination of choices of the main components was similar to that used in the construction of recombinant baculovirus in Example 1, and was show below:

Cap-LinkA-(ITR-GFP)-linkB-Rep

The ITR-GFP was linked by a ligation nucleic acid segment between the P10 and PH promoter in a pFBD vector by conventional molecular cloning, to construct a recombinant shuttle plasmid pFBD/Cap-(ITR-GFP)-Rep, as shown in FIG. 2C.

Following the operation process of a Bac to Bac system, BmDH10Bac strain containing the BmNPV baculovirus genome was transformed with the recombinant shuttle plasmid. A recombinant baculovirus genome (Bacmid) was obtained by Tn7 transposon-mediated recombination. Positive strains containing recombinant Bacmid were obtained by blue-white spot screening and PCR identification. The recombinant Bacmid was purified by extraction, with which BmN cells in adherent culture was transfected. The insect cells were gradually completely infected by the recombinant baculovirus produced after transfection and displayed obvious cytopathogenic effect (CPE). The cell culture was centrifuged for 5 min at 3000 rpm, and the supernatant contained the produced recombinant baculovirus (BEV).

Figure 7A:
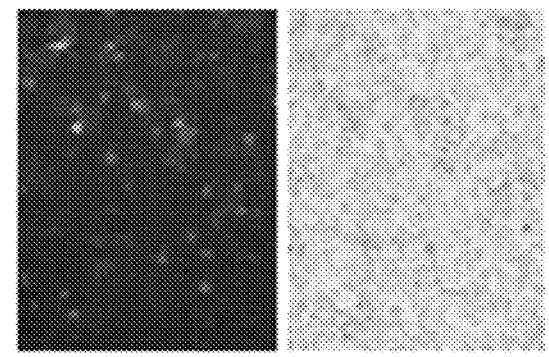
FIG. 7A is fluorescence microscopic images of BmN cells infected with the recombinant baculovirus BEV/Cap-(ITR-GFP)-Rep in Example 2.
Figure 7A:
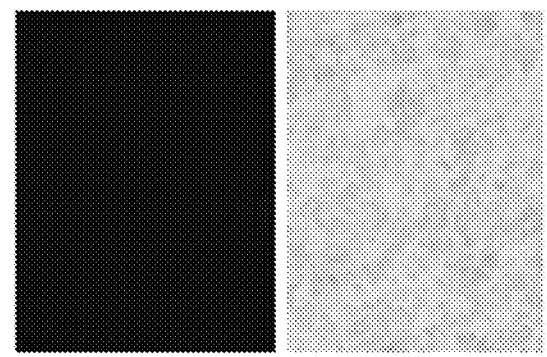

BmN cells in adherent culture were infected with the supernatant and then cultured for 3 days. It was observed that the non-infected BmN cells in the control group grew normally, and no GFP was expressed. In contrast, in the test group, obvious cytopathogenic effect (CPE) occurred to the BmN cells infected with BEV, and GFP expression was obvious, as shown in FIG. 7A. This suggested that the BEV was successfully produced through the above scheme. The cultured BmN cells were further infected with BEV produced after transfecting the BmN cells, and obvious CPE occurred to the cells 3 days after infection. The cell culture was centrifuged for 5 min at 3000 rpm, and the BEV supernatant was obtained. The BEV titer was determined by quantitative fluorescent PCR, as described in ProcNatlAcadSci USA, 2009. 106 (13): p. 5059-64.

The cultured BmN cells were infected with the BEV produced in Example 2 at a multiplicity of infection (MOI) of 5. Three days after infection, the culture supernatant and cells were collected separately. The BEV was mainly secreted and released into the culture supernatant, and some un-released BEV was also present in BmN cells. The rAAV was mainly present in the cell nucleus. Since CPE occurred after the insect cells were infected and some cells were lysed, rAAV was also partly released into the supernatant. Therefore, BEV and rAAV were present in both the supernatant and the cells.

Figure 7B:
FIG. 7B is fluorescence microscopic images of HEK293 and BmN cells infected with the rAAV produced in Example 2.

To verify that active rAAV was produced by infecting BmN cells with the recombinant baculovirus, the production of rAAV with the system was experimentally confirmed by HEK293 cells and Sf9 cells based infection assays. The experimental results are shown in FIG. 7B. The specific implementation process and the result analysis were as follows. The cell pellets were subjected to 3 rounds of repeated freezing and thawing, and then lysed. The cell lysate supernatant was collected by centrifugation for 5 min at 5000 rpm. The rAAV was non-enveloped, and the activity was not affected after 30 min-treatment at 60° C.; and the recombinant baculovirus (BEV) was enveloped, and deactivated after 30 min-treatment at 60° C. A simple infection-based method was used to test the rAAV activity (FIG. 7B). For rAAV2 (293 cells derived) samples, in 293 cells-based infection assays, both the treated and untreated can express GFP. In BmN cells-based infection assays, both the treated and untreated cannot express GFP, it indicates that rAAV2 do not infect BmN cells. For BEV/Cap-(ITR-GFP)-Rep supernatant samples, which contain the major secreted BEV and some rAAV. In 293 cells-based infection assays, both the treated and untreated can express GFP, while the GFP expression of the treated decrease significantly, because inactive BEV do not express GFP and only some rAAV can express GFP. In BmN cells-based infection assays, the untreated can express GFP, but the treated cannot express GFP. For BEV/Cap-(ITR-GFP)-Rep infected BmN cells lysate supernatant samples, which contain some non-secret BEVs and the major rAAV. In 293 cells-based infection assays, both the treated and untreated can express GFP, but GFP expression of the treated decrease slightly. It indicates that there is large amount of rAAVs expressing GFP. In BmN cells-based infection assays, the untreated can express GFP, while the treated cannot express GFP (FIG. 7B).

The results shown in FIG. 7A indicate that rAAV can be produced by infecting BmN cells with the recombinant baculovirus BEV/Cap-(ITR-GFP)-Rep.

(2) Production of rAAV by Infecting Silkworm Larvae with Recombinant Baculovirus (BEV)

Figure 8:
FIG. 8 shows morphologies of normal silkworm larvae and silkworm larvae having obvious pathological changes after infection with a recombinant baculovirus in Example 2.
Figure 8:

Hatched silkworm larvae were fed to 4-5th instar larvae. The larvae were anesthetized on ice, and inoculated by subcutaneously injecting about 20 μL recombinant baculovirus (with a BEV titer of about 1×10$^7$ VG/mL) using a micro-syringe. Then, the larvae were cultured in a culture dish with a lid, and fed for additional 6-7 days. The infected silkworm larvae had obvious pathologic symptom changes, such as appetite loss, slow movement and swollen somite. The un-infected silkworm larvae grew normally, as shown in FIG. 8.

(3) Lysis of Larvae, Purification and Activity Verification of rAAV

The collected larvae were mashed and ground, added with a PBS solution, and homogenized, followed by 3 rounds of repeated freezing and thawing. After centrifugation for 10 min at 5000 rpm, the larvae lysate supernatant was collected. After the silkworm larvae were infected with BEV, rAAV was produced in the larvae cells while BEV was multiplied. Both BEV and rAAV were present in the larvae lysate supernatant.

Figure 9A:
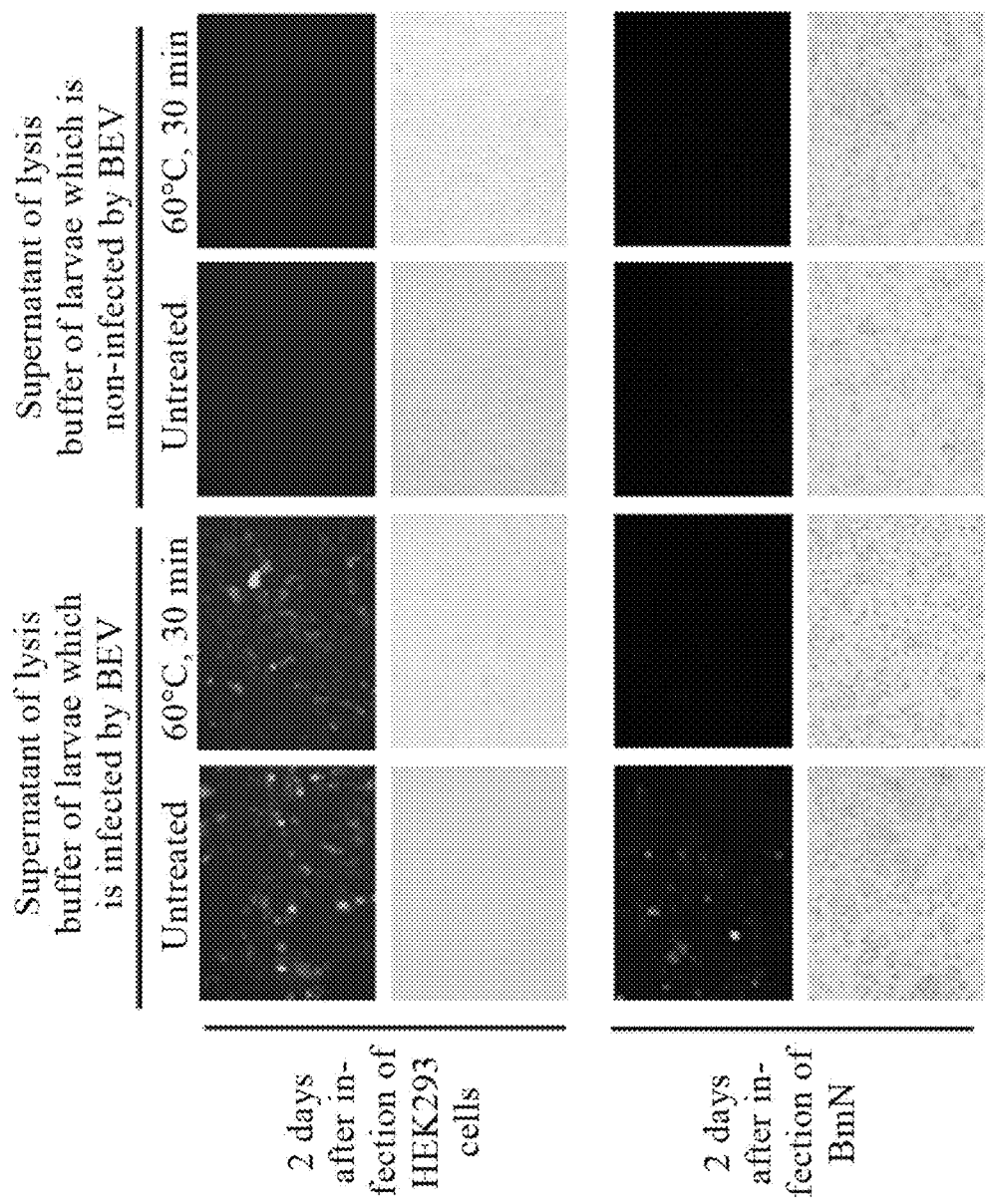
FIG. 9A is fluorescence microscopic images of HEK293 and BmN cells infected with a larvae lysate supernatant in Example 2.

To verify that rAAV was produced by infecting silkworm larvae by injecting the recombinant baculovirus, the production of rAAV was experimentally confirmed by HEK293 cells and BmN cells based infection assays. The experimental results are shown in FIG. 9A. Given the fact that rAAV was non-enveloped, and the activity was not affected after 30 min-treatment at 60° C.; and the recombinant baculovirus (BEV) was enveloped, and deactivated after 30 min-treatment at 60° C., the specific implementation process and the result analysis were as follows.

For the crude uninfected larvae lysate supernatant samples, in both 293 and BmN cells-based infection assays, there are no GFP expression (FIG. 9A). For the crude infected larvae lysate supernatant samples, in 293 cells-based infection assays, both the treated and untreated can express GFP, but GFP expression of the treated decrease slightly. It indicates that there is large amount of rAAVs expressing GFP. In BmN cells-based infection assays, the untreated can express GFP, but the treated cannot express GFP (FIG. 9A).

Figure 9B:
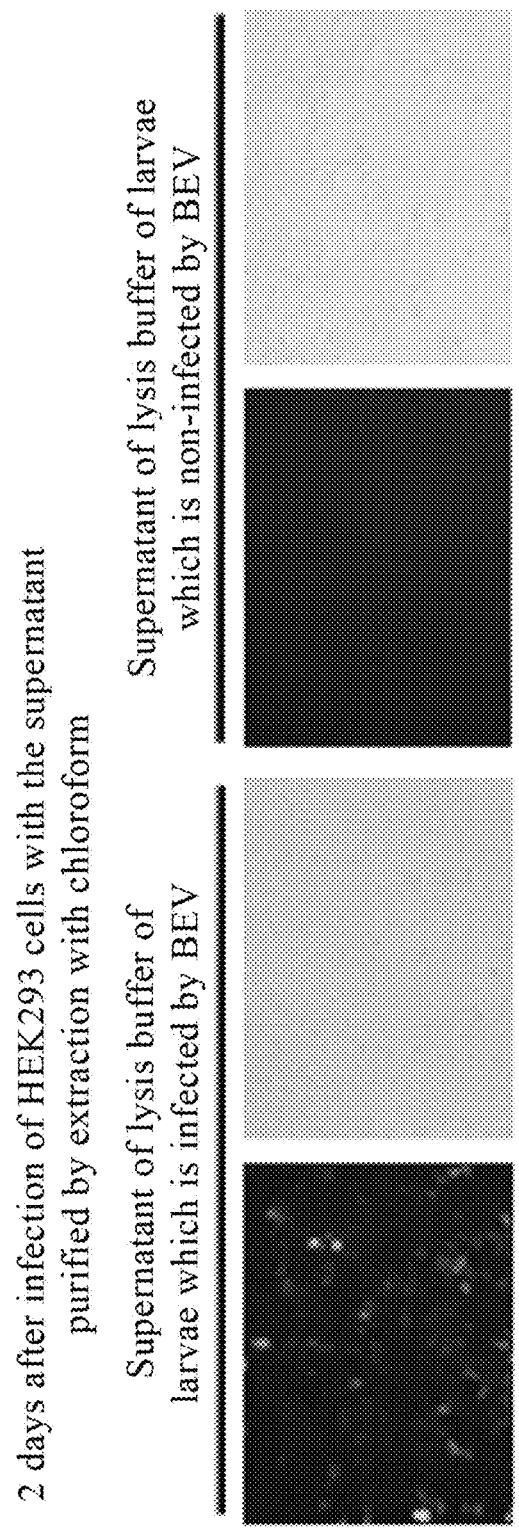
FIG. 9B is fluorescence microscopic images of HEK293 cells infected with a larvae lysate supernatant purified by extraction with chloroform in Example 2.

Similar to the difference in thermo-stability, the differences in chloroform tolerance between enveloped BEV and non-enveloped AAV allowed the specific inactivation of BEV by chloroform extraction treatment. The crude larvae lysate supernatant samples were subject to chloroform extraction for 3 times. In 293 cells-based infection assays, the infected samples can express GFP, and the uninfected cannot express GFP. This result suggests that the infected samples contain rAAV tolerable for chloroform extraction treatment (FIG. 9B).

The above results showed that active rAAV was successfully prepared by infecting silkworm larvae with the recombinant baculovirus BEV/Cap-(ITR-GFP)-Rep.

Unless otherwise indicated, the numerical ranges involved in the invention include the end values. While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for producing recombinant adeno-associated virus, the method comprising:
    (1) transforming a gene of interest (GOI) into a recombinant baculovirus, wherein the recombinant baculovirus has a genome integrated with AAV Rep gene, Cap gene, and rAAV genome ITR-GOI; and the ITR-GOI is linked to expression cassette of the Cap gene and the Rep gene by a 5' terminal nucleic acid segment or a 3' terminal nucleic acid segment of the ITR-GOI; and the 5' terminal nucleic acid segment or the 3' terminal nucleic acid segment is a ligation nucleic acid sequence having a length ranging from 80 to 140 bp;
    (2) infecting host insect larvae with the recombinant baculovirus prepared in (1) to produce the rAAV in vivo in the host insect larvae; and
    (3) lysing the host insect larvae obtained in (2), and extracting and purifying the rAAV,
    wherein the infecting host insect larvae with the recombinant baculovirus prepared in (1) to produce the rAAV in vivo in the host insect larvae comprises:
    (2-1-1): feeding hatched host insect larvae to between a 4th instar stage and a 5th instar stage;
    (2-1-2): inoculating the host insect larvae obtained in (2-1-1) by subcutaneously injecting 10-20 μL, of the recombinant baculovirus at a titer of $1 \times 10^7$ VG/mL to $1 \times 10^9$ VG/mL prepared in (1); and
    (2-1-3): feeding the host insect larvae injected with the recombinant baculovirus obtained in (2-1-2) until the larvae have the symptoms of appetite loss, sluggish movement, and swollen somite, and then stopping feeding, and harvesting the larvae.

2. The method of claim 1, wherein in (2-1-3), the feeding is stopped when the symptoms occur in 3 to 7 days after the host insect larvae are infected with the recombinant baculovirus.

3. The method of claim 1, wherein the recombinant baculovirus includes part of genome sequence of *Autographa californica* multiple nuclear polyhedrosis virus (AcMNPV) (Genbank accession No.: KM667940.1 or NC_001623.1) or *Bombyx mori* nucleopolyhedrovirus (Bm-NPV) (Genbank accession No.: L33180.1).

4. The method of claim 1, wherein the host insect larvae are larvae of beet armyworm or silkworm.

5. The method of claim 1, wherein in (3), the lysing of the host insect larvae comprises: mashing and grinding the host insect larvae, adding a PBS solution, homogenizing, freezing, and then thawing, to prepare the lysate.

6. The method of claim 1, wherein in (3), the step of extracting and purifying the rAAV comprises: centrifuging the lysate after the host insect larvae is lysed, collecting the supernatant, and extracting with chloroform, to obtain a preliminarily purified rAAV.

* * * * *